(12) United States Patent
Jo (10) Patent No.: US 12,115,907 B2
(45) Date of Patent: Oct. 15, 2024

(54) INDOOR LIGHT CONTROL SYSTEM AND CONTROL METHOD THEREOF

(71) Applicant: HYUNDAI MOBIS CO., LTD., Seoul (KR)

(72) Inventor: Pyeong Geun Jo, Suwon-si (KR)

(73) Assignee: HYUNDAI MOBIS CO., LTD., Seoul (KR)

( * ) Notice: Subject to any disclaimer, the term of this patent is extended or adjusted under 35 U.S.C. 154(b) by 34 days.

(21) Appl. No.: 18/146,208

(22) Filed: Dec. 23, 2022

(65) Prior Publication Data

US 2023/0278491 A1 Sep. 7, 2023

(30) Foreign Application Priority Data

Mar. 2, 2022 (KR) .......................... 10-2022-0026841

(51) Int. Cl.
*B60Q 3/80* (2017.01)
*B60Q 3/70* (2017.01)
*G06V 10/141* (2022.01)
*G06V 20/59* (2022.01)
*G06V 40/16* (2022.01)
*G06V 40/18* (2022.01)

(52) U.S. Cl.
CPC ................. *B60Q 3/80* (2017.02); *B60Q 3/70* (2017.02); *G06V 10/141* (2022.01); *G06V 20/593* (2022.01); *G06V 40/171* (2022.01); *G06V 40/18* (2022.01)

(58) Field of Classification Search
None
See application file for complete search history.

(56) References Cited

U.S. PATENT DOCUMENTS

| | | | |
|---|---|---|---|
| 2021/0261050 A1* | 8/2021 | Sobhany | B60Q 3/80 |
| 2022/0118985 A1* | 4/2022 | Austin | B60W 40/09 |
| 2022/0121865 A1* | 4/2022 | Austin | G06V 40/193 |
| 2022/0153302 A1* | 5/2022 | Arechiga-Gonzalez | ........ B60W 50/14 |
| 2023/0054024 A1* | 2/2023 | Oba | A61B 5/18 |
| 2023/0065399 A1* | 3/2023 | Ren | G16H 30/40 |
| 2023/0219495 A1* | 7/2023 | Takamatsu | B60Q 3/735 315/77 |
| 2023/0316783 A1* | 10/2023 | Hödlmoser | G06V 20/64 382/104 |

FOREIGN PATENT DOCUMENTS

KR 20-0303691 2/2003

OTHER PUBLICATIONS

English Language Abstract of KR 20-0303691 published Feb. 12, 2003.

* cited by examiner

*Primary Examiner* — Wilson Lee
(74) *Attorney, Agent, or Firm* — DLA Piper LLP US (57) ABSTRACT

An indoor light control system and a control method thereof, and more particularly, an indoor light control system that calculates a sight line direction of a driver through facial posture analysis data of the driver and controls an indoor light to be activated or deactivated according to the sight line direction, and a control method thereof.

20 Claims, 9 Drawing Sheets

INDOOR LIGHT CONTROL SYSTEM AND CONTROL METHOD THEREOF

CROSS-REFERENCE TO RELATED APPLICATIONS

This application claims priority under 35 U.S.C. § 119 to Korean Patent Application No. 10-2022-0026841, filed on Mar. 2, 2022, in the Korean Intellectual Property Office, the disclosure of which is incorporated herein by reference in its entirety.

TECHNICAL FIELD

The following disclosure relates to an indoor light control system and a control method thereof, and more particularly, to an indoor light control system that calculates a sight line direction of a driver through facial posture analysis data of the driver and controls an indoor light to be activated or deactivated according to the sight line direction, and a control method thereof.

BACKGROUND

An indoor light of a vehicle serves as an interior illumination for occupants in the vehicle including a driver. It is mainly used by the driver to find an object when the inside of the vehicle is dark.

To operate the indoor light, the driver needs to manually operate a switch on a console overhead. The manual operation of the indoor light is not complicated work, but may be inconvenient for the driver when the driver is driving or needs to look inside the vehicle in a sudden situation.

In addition, if the indoor light is continuously turned on due to a driver's mistake, a battery may be discharged. Also, if the indoor light is turned on during driving at night, it may be difficult to see the outside of the vehicle because the driver gazes at the outside of the vehicle, which is relatively darker than the inside of the vehicle, from the inside of the vehicle.

In addition, if the inside of the vehicle is bright, the driver's view may be further restricted because light inside the vehicle is reflected by a windshield.

Therefore, there is a demand for developing an indoor light control system capable of automatically turning on/off an indoor light by analyzing a sight line direction of a driver without a separate driver's operation.

RELATED ART DOCUMENT

Patent Document

Korean Utility Model No. 20-0303691 (Issued on Jan. 28, 2003)

SUMMARY

An embodiment of the present invention is directed to providing an indoor light control system capable of calculating facial posture analysis data and sight line direction of a driver through captured indoor image data from a camera unit, and automatically controlling an indoor light based on the sight line direction of the driver, and a control method thereof.

Another embodiment of the present invention is directed to providing an indoor light control system capable of controlling an indoor light according to various environmental conditions in the vehicle as well as a sight line direction of a driver, and a control method thereof.

In one general aspect, an indoor light control system for controlling at least one indoor light provided in the vehicle indoors includes: a camera unit providing captured indoor image data of the vehicle; and a control unit controlling the indoor light based on the captured indoor image data, wherein the control unit calculates a sight line direction of a driver who sits on a driver's seat based on the captured indoor image data, and controls the indoor light according to the sight line direction of the driver.

The control unit may extract feature points in a face region of the driver based on the captured indoor image data, calculate facial posture analysis data including at least one of yawing, pitching, and rolling of a face based on the extracted feature points, and calculate a sight line direction of the driver based on the facial posture analysis data.

The control unit may calculate a forward direction of the face as the sight line direction of the driver based on the calculated facial posture analysis data.

The control unit may calculate pupil direction data of the driver based on the captured indoor image data, and calculate a sight line direction of the driver based on the calculated facial posture analysis data and pupil direction data.

The control unit may control the indoor light to an activation mode when the sight line direction deviates from a boundary line of a front window on one side of the vehicle, and control the indoor light to a deactivation mode when the sight line direction returns to a region within the front window of the vehicle.

When an illuminance in the vehicle is higher than a set reference illuminance, even if the sight line direction deviates from the boundary line of the front window on one side of the vehicle, the control unit may control the indoor light to the deactivation mode.

When a turn signal lamp on one side of the front window of the vehicle is turned on, and the sight line direction is in a region within a side mirror on the one side of the front window of the vehicle, the control unit may control the indoor light to the deactivation mode.

The control unit may determine whether or not there is an occupant on a front passenger seat based on at least one of the captured indoor image data or seat weight sensing data, and control the indoor light to the deactivation mode when the sight line direction is within a preset front passenger seat direction range in a case where there is an occupant on the front passenger seat.

When a driving speed of the vehicle is higher than a set first reference speed, the control unit may control the indoor light to the deactivation mode.

When the sight line direction deviates from the boundary line of the front window on one side of the vehicle, the driving speed of the vehicle is higher than a set second reference speed, and an obstacle is detected in a driving direction of the vehicle, the control unit may control the indoor light to a warning mode, and the second reference speed may be equal to or lower than the first reference speed.

A control method of the indoor light control system includes: a) calculating, by the control unit, facial posture analysis data based on captured indoor image data from the camera unit; b) calculating, by the control unit, a sight line direction of the driver based on the facial posture analysis data; and c) controlling, by the control unit, the indoor light based on the sight line direction, such that the indoor light is controlled to an activation mode when the sight line direction deviates from a boundary line of a front window on one side of the vehicle, and the indoor light is controlled to a deactivation mode when the sight line direction is in a region within the front window of the vehicle.

The step a) may include: a1) extracting, by the control unit, feature points in a face region of the driver based on the captured indoor image data; and a2) calculating, by the control unit, facial posture analysis data including at least one of yawing, pitching, and rolling of a face based on the extracted feature points.

The step b) may include: b1) calculating, by the control unit, pupil direction data of the driver based on the captured indoor image data; and b2) calculating, by the control unit, a sight line direction of the driver based on the calculated facial posture analysis data and pupil direction data.

The control method may further include, after controlling the indoor light to the activation mode in the step c), d) controlling, by the control unit, the indoor light to the deactivation mode when the sight line direction returns to the region within the front window of the vehicle.

In the step c), while the sight line direction deviates from the boundary line of the front window on one side of the vehicle, when an illuminance in the vehicle is higher than a set reference illuminance or when a driving speed of the vehicle is higher than a set first reference speed, the control unit may control the indoor light to the deactivation mode.

In the step b), the control unit calculates a forward direction of the face as the sight line direction of the driver based on the calculated facial posture analysis data.

In the step c), while the sight line direction deviates from the boundary line of the front window on one side of the vehicle, when a turn signal lamp on one side of the front window of the vehicle is turned on, and the sight line direction is in a region within a side mirror on the one side of the front window of the vehicle, the control unit controls the indoor light to the deactivation mode.

In the step c), while the sight line direction deviates from the boundary line of the front window on one side of the vehicle, when there is an occupant on a front passenger seat as a result of determining whether or not there is an occupant on a front passenger seat based on the captured indoor image data or seat weight sensing data, and the sight line direction is within a preset front passenger seat direction range, the control unit controls the indoor light to the deactivation mode.

In the step c), while the sight line direction deviates from the boundary line of the front window on one side of the vehicle, when the driving speed of the vehicle is higher than a set second reference speed, and an obstacle is detected in a driving direction of the vehicle, the control unit controls the indoor light to a warning mode, and the second reference speed is equal to or lower than the first reference speed.

In another general aspect, a computer-readable recording medium records a program for executing the above-described method.

According to the present invention, the indoor light can be turned on automatically when the driver turns his/her face to look at a front passenger seat or a rear seat. Therefore, the indoor light can be turned on conveniently without a separate process of operating the indoor light. Also, a time required for operating the indoor light can be eliminated, so that the user can check the front passenger seat or the rear seat as quickly as possible. Therefore, stability can also be improved.

In addition, by controlling the indoor light in consideration of various environmental conditions in the vehicle as well as the sight line direction of the driver, the driver can be induced not to look elsewhere other than ahead in a dangerous situation.

DETAILED DESCRIPTION OF MAIN ELEMENTS

100: Camera unit
200: Control unit
210: Activation mode
220: Deactivation mode
230: Warning mode
240: Color temperature adjustment mode
300: Sensor unit
310: First sensing unit
320: Second sensing unit
330: Third sensing unit
340: Fourth sensing unit
400: User input unit
500: Indoor light
1000: Indoor light control system
SL: Sight line direction
FW: Front window of vehicle

DETAILED DESCRIPTION OF EMBODIMENTS

Hereinafter, preferred embodiments of the present invention will be exemplified and referred to so as to describe the present invention, operational advantages of the present invention, and objects to be achieved by implementing the present invention.

Figure 1:
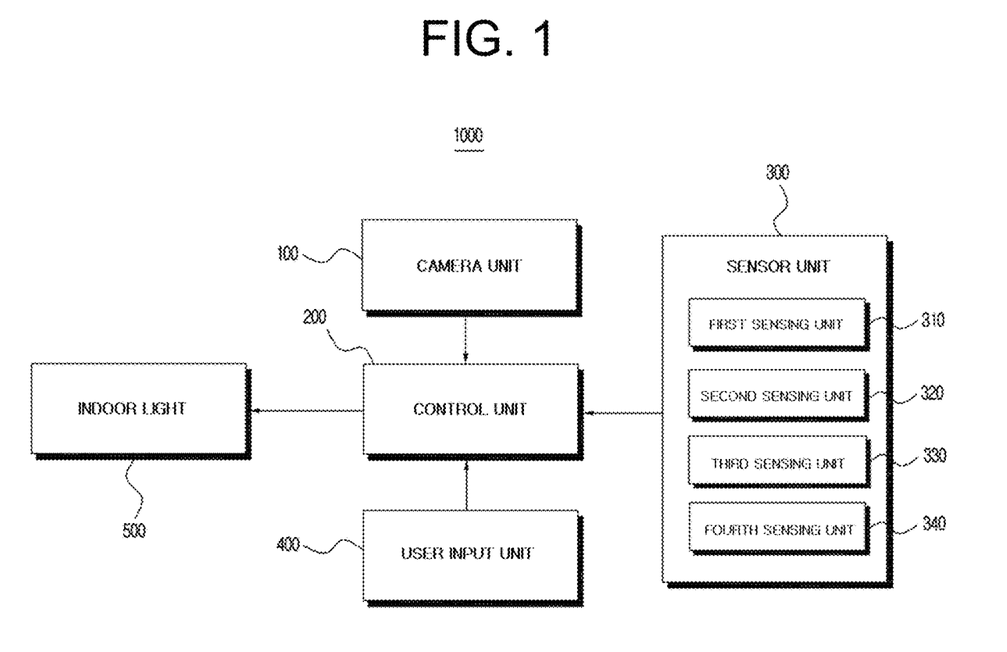
FIG. 1 is a block diagram illustrating a configuration of an indoor light control system according to an embodiment of the present invention.
Figure 2:
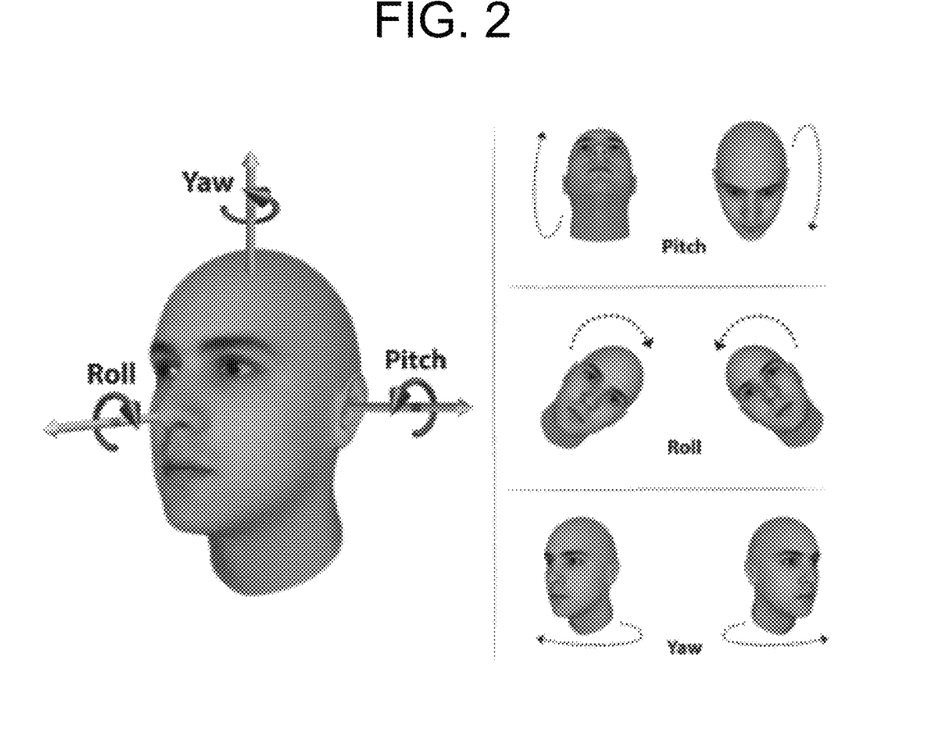
FIG. 2 is a diagram for explaining yawing, pitching, and rolling for calculating facial posture analysis data according to an embodiment of the present invention.
Figure 3A:
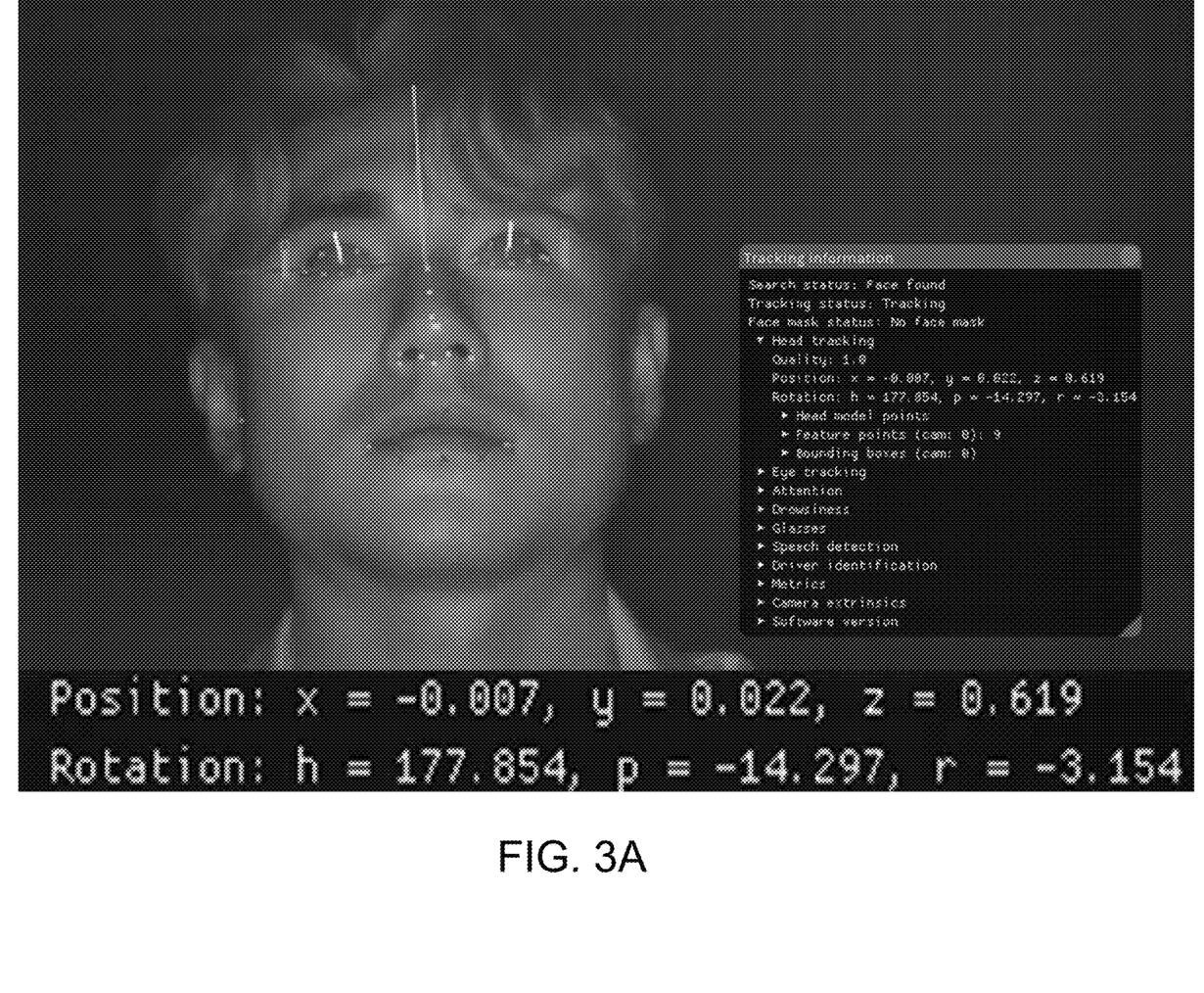
FIGS. 3A and 3B are diagrams illustrating a state in which facial posture analysis data is being calculated according to an embodiment of the present invention.
Figure 3B:
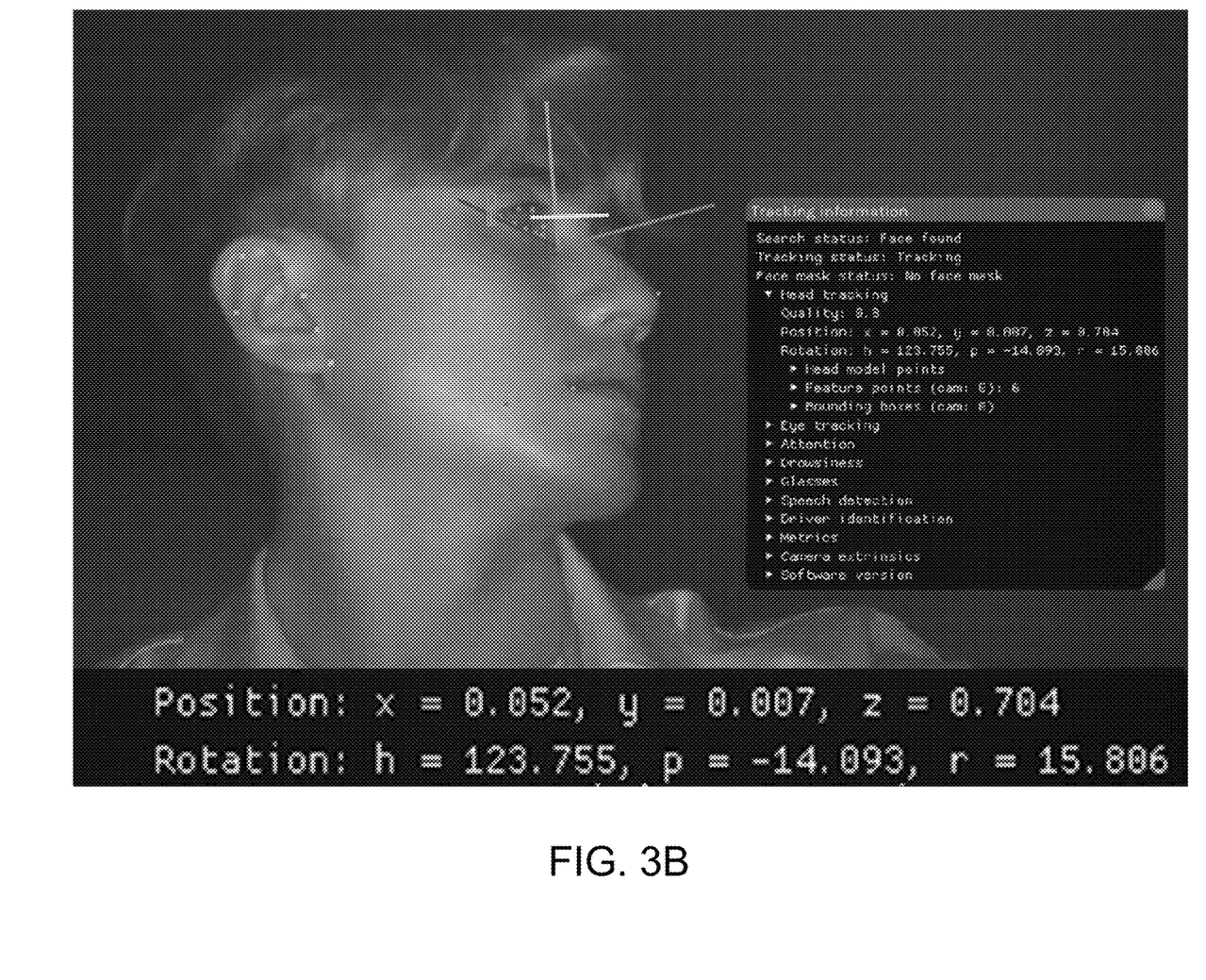

FIG. 1 is a block diagram illustrating a configuration of an indoor light control system according to an embodiment of the present invention, FIG. 2 is a diagram for explaining yawing, pitching, and rolling for calculating facial posture analysis data according to an embodiment of the present invention, and FIGS. 3A and 3B are diagrams illustrating a state in which facial posture analysis data is being calculated according to an embodiment of the present invention.

Figure 4:
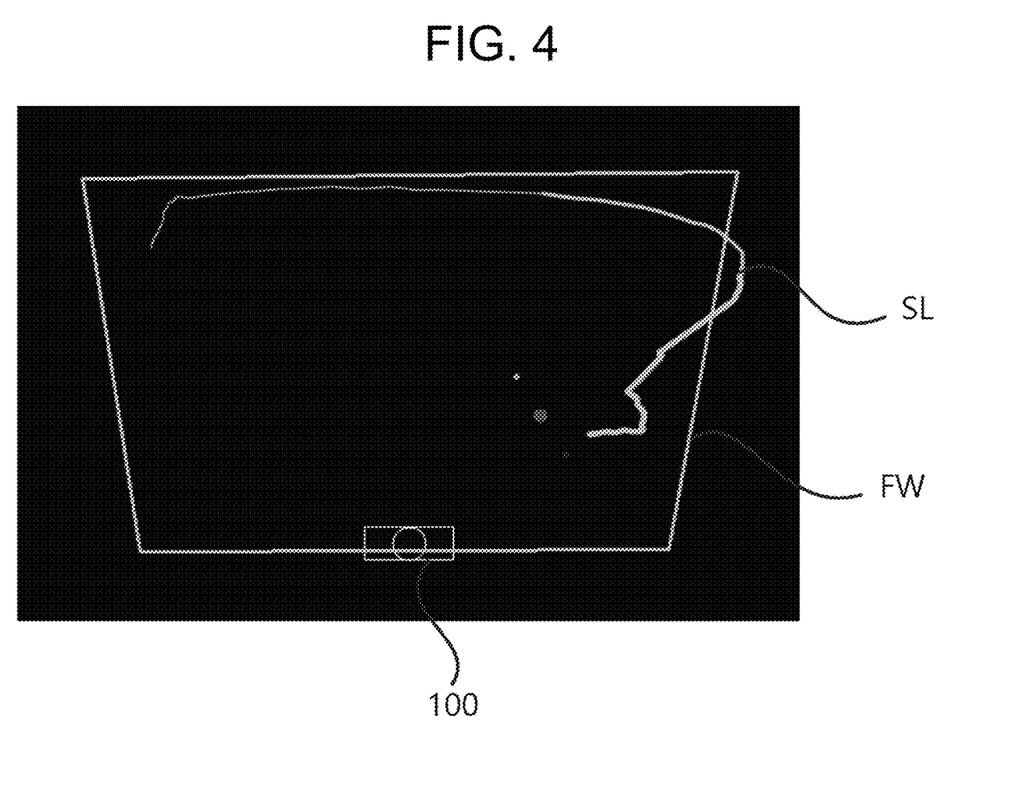
FIG. 4 is a diagram illustrating a state in which a sight line direction is being calculated according to an embodiment of the present invention.
Figure 5:
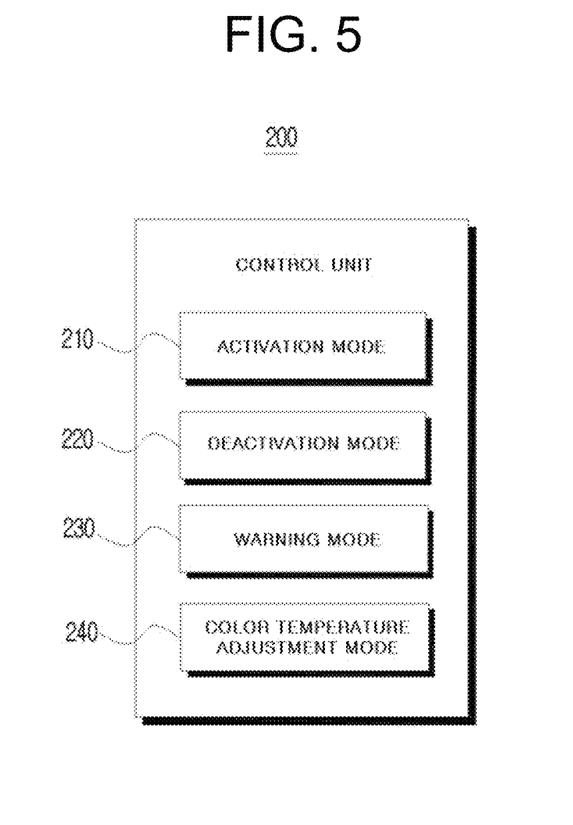
FIG. 5 is a block diagram illustrating control modes of a control unit according to an embodiment of the present invention.

In addition, FIG. 4 is a diagram illustrating a state in which a sight line direction is being calculated according to an embodiment of the present invention, and FIG. 5 is a block diagram illustrating control modes of a control unit according to an embodiment of the present invention.

Referring to the drawings, an indoor light control system 1000 according to an embodiment of the present invention largely includes a camera unit 100 providing captured indoor image data of a vehicle, and a control unit 200 calculating a sight line direction SL of a driver who sits on a driver's seat and controlling an indoor light 500 according to the sight line direction SL of the driver.

Here, the camera unit 100 is installed at a set position in the vehicle to generate captured indoor image data and provide the generated captured indoor image data to the control unit 200. The camera unit 100 may be installed at one location, or a plurality of camera units 100 may be installed to be spaced apart from each other in the vehicle to each generate captured indoor image data within a capturing range.

In a case where the camera unit 100 is installed at one location, the camera unit 100 may be installed at a cluster or a steering column to capture a front image of the driver, or may be installed at an upper end of a control pad (C-Pad) as illustrated in FIG. 3A, 3B or 4 to capture an image of the driver.

However, in order to more precisely control the indoor light 500 and in consideration of various indoor environments in the vehicle, a plurality of camera units 100 may be installed. For example, cameras for capturing images of the driver may be installed at two or more locations, a camera capable of calculating whether there is an occupant on a front passenger seat may be added to the upper end of the C-Pad in front of the front passenger seat, or a camera capable of calculating whether there is an occupant on a rear passenger seat may be added on one side of the rear of the vehicle, on the ceiling of the vehicle, or the like.

Here, the plurality of cameras capturing images of the driver may convert a facial posture of the driver into 3D coordinates using the captured indoor image data, making it possible to more precisely calculate a sight line direction of the driver.

In addition, the cameras are preferably IR cameras to smoothly capture images of indoor environments including the driver both by day and by night.

Meanwhile, as described above, the control unit 200 is provided to calculate a sight line direction SL of the driver based on the captured indoor image data received from the camera unit 100, and control the indoor light 500 to one of an activation mode, a deactivation mode, and a warning mode according to the calculated sight line direction. Here, the control unit 200 extracts feature points in a face region of the driver based on the captured indoor image data to calculate a sight line direction of the driver, calculates facial posture analysis data including at least one of yawing, pitching, and rolling of a face based on the extracted feature points, and calculates a sight line direction SL of the driver based on the calculated facial posture analysis data.

As described above, depending on how many camera units 100 are installed and where the camera units 100 are installed, captured indoor image data may vary, and accordingly, a process of calculating facial posture analysis data of the driver may vary. In order to more accurately and precisely analyze a facial posture, it is preferable to install a plurality of camera units 100.

In addition, the feature points in the face region include at least both eyes, a center point between the eyes, a center point of a nose, and opposite endpoints of a mouth. The control unit 200 detects feature points in the face region from the captured indoor image data, and sets positions of the feature points when the driver gazes straight ahead as reference 3D positions based on relative positions of the feature points.

In order to determine relative positions of feature points on captured indoor image data detected thereafter, as illustrated in FIG. 2, the control unit 200 calculates at least one of an angle at which the driver's face rotates about an X axis (a pitching angle), an angle at which the driver's face rotates about a Y axis (a yawing angle), and an angle at which the driver's face rotates about a Z axis (a rolling angle).

Furthermore, if necessary, the control unit 200 may additionally consider distances of parallel movements from the reference position to the feature points with respect to the X axis, the Y axis, and the Z axis, when calculating facial posture analysis data.

If necessary, such a process of calculating facial posture analysis data may be performed more precisely by learning changes in facial posture according to changes in respective coordinates of feature points through machine learning.

Based on the facial posture analysis data calculated as described above, the control unit 200 calculates a sight line direction SL of the driver in a current facial posture, as illustrated in FIG. 4, to perform an activation mode 210, a deactivation mode 220, or a warning mode 230 of the indoor light 500 according to the calculated sight line direction.

Here, the activation mode 210 is a control mode in which the indoor light 500 is turned on according to a set color temperature, and the deactivation mode 220 is a control mode in which the indoor light 500 in a turn-on state is turned off or the indoor light 500 in a turn-off state remains continuously turned off.

In addition, the warning mode 230 is a control mode in which the indoor light 500 is repeatedly turned on and off at predetermined intervals to notify the driver that a current situation is a dangerous or cautionary situation.

Further, the indoor light control mode of the control unit 200 may include a color temperature adjustment mode 240 in which the indoor light 500 is turned on, with a color temperature of the indoor light varying according to settings.

In order to perform the color temperature adjustment mode 240, it is required that the indoor light 500 include a plurality of light emitting units having different color temperatures or include a single light emitting unit capable of emitting light at a plurality of color temperatures.

Through such a color temperature adjustment mode 240, the indoor light 500 may be turned on at a preset color temperature preferred by the driver or at a color temperature designated for a preset situation.

Meanwhile, as another embodiment of the present invention for calculating a sight line direction SL of the driver, in addition to the calculation of the facial posture analysis data of the driver as described above, pupil direction data of the driver may be calculated. Based on both the facial posture analysis data of the driver and the pupil direction data of the driver, a sight line direction of the driver may be calculated.

This is because the driver may gaze in a specific sight line direction through his/her pupils in a state where his/her face does not greatly rotate in one direction. Therefore, in order to more accurately calculate a sight line direction of the driver, the pupil direction data is added when the sight line direction is calculated.

To this end, the process of calculating a sight line direction of the driver may include calculating facial posture analysis data to estimate a forward sight line direction according to a current facial posture of the driver, and calculating a final sight line direction by considering pupil direction data in the forward sight line direction.

Meanwhile, the control unit 200 controls the indoor light 500 to one of the plurality of modes according to the sight line direction SL of the driver calculated as described above.

Hereinafter, the mode control of the control unit 200 according to the sight line direction will be described.

First, the activation mode 210 is performed by the control unit 200 when the sight line direction SL of the driver deviates from a boundary line of a front window FW on one side of the vehicle as illustrated in FIG. 4 according to an embodiment of the present invention.

That is, the present invention is to further improve user convenience by activating the indoor light, that is, turning on the indoor light, without a separate driver's operation, when the driver's sight line is directed toward a front passenger's seat or a rear seat of the vehicle, and to improve driving stability by eliminating a time required for the driver to operate the indoor light.

As an example of a setting, when the sight line direction of the driver deviates from the boundary line of the front window FW on one side of the vehicle, it is determined that the driver is looking at something on the front passenger seat or the rear seat, and the indoor light is turned on.

Here, the boundary line of the front window FW on one side of the vehicle may be set to a right boundary line when the driver is located on a front left seat as in Korea, or may be set to a left boundary line when the driver is located on a front right seat as in Japan.

As another example of a setting, when the sight line direction of the driver deviates from a pillar on one side of the vehicle, the control unit may control the indoor light to the activation mode 210. Furthermore, when the sight line direction of the driver is within a boundary line of a side window near the passenger seat of the vehicle or deviates rearward from the boundary line of the side window near the passenger seat of the vehicle, the control unit may control the indoor light to the activation mode 210.

In a state where the control unit 200 controls the indoor light 500 to the activation mode 210 because the sight line direction of the driver deviates from a set standard (such as the boundary line of the front window or the pillar on one side of the vehicle), when the sight line direction of the driver returns to the set standard, the control unit 200 controls the indoor light 500 back to the deactivation mode 220.

Here, as described above, the deactivation mode 220 is a control mode in which the indoor light 500 in a turn-on state is turned off or the indoor light 500 in a turn-off state remains continuously turned off.

The deactivation mode 220 is performed by the control unit 200 when the sight line direction SL of the driver is within the set standard. However, in the present invention, even when the sight line direction of the driver deviates from the set standard, the deactivation mode 220 may be performed.

As an example, when the control unit 200 receives illuminance information from a first sensing unit 310 for sensing an illuminance in the vehicle and the illuminance in the vehicle is higher than a set reference illuminance, even if the sight line direction SL of the driver deviates from the boundary line of the front window on one side of the vehicle, the control unit 200 controls the indoor light to the deactivation mode 220.

This is to turn on the indoor light when an indoor illuminance is low at night or due to cloudy weather, and not to turn on the indoor light when an indoor illuminance is higher than the preset reference illuminance, such as during daytime.

Here, the first sensing unit 310 may be an illuminance sensor installed in the vehicle.

As another example, the control unit 200 may be configured to receive turn signal lamp turn-on information from a second sensing unit 320 for providing turn signal lamp turn-on information of the vehicle. In this case, when a turn signal lamp on one side of the front window of the vehicle is turned on, and the sight line direction of the driver is in a region within a side mirror on one side of the front window of the vehicle, the control unit 200 controls the indoor light to the deactivation mode 220.

That is, when a turn signal lamp on one side (on a right side in a case where the driver is on the left seat) is turned on as described above, even if the sight line direction of the driver deviates from the set standard (such as the boundary line of the front window or the pillar on one side of the vehicle), the sight line of the driver is generally directed to see a side mirror on one side, and thus, the control unit 200 controls the indoor light to the deactivation mode 220.

The second sensing unit 320 may be a vehicle body management unit for managing whether or not a turn signal lamp in the vehicle is turned on, such as a body domain controller (BDC).

As another example, the control unit 200 determines whether or not there is an occupant on the front passenger seat based on captured indoor image data or seat weight sensing data. In a case where there is an occupant on the front passenger seat, when the sight line direction of the driver is within a preset front passenger seat direction range, the control unit 200 controls the indoor light 500 to the deactivation mode 220.

This is because the driver's sight line may be temporarily directed toward the front passenger seat during conversation in a case where there is an occupant on the front passenger seat, and thus, the control unit 200 does not control the indoor light 500 to the activation mode 210.

In addition, in a case where there is an occupant on the front passenger seat, the occupant on the front passenger seat may operate the indoor light. Therefore, in that case, it is preferable that the control unit 200 controls the indoor light to the deactivation mode 220 for safe driving.

Here, the captured indoor image data may be transmitted from the camera unit 100 to the control unit 200 for determination, and the seat weight sensing data may be transmitted from a weight sensor installed on one side of the seat to sense a weight of the occupant sitting on the seat.

The weight sensor may be, for example, a seat belt reminder (SBR). The SBR sensor is installed on a lower center side of the seat to sense a force applied from the seat, generate seat weight sensing data, and then transmit the seat weight sensing data to the control unit 200.

When the seat weight obtained as described above is larger than a preset reference weight, the control unit 200 determines that there is an occupant on the front passenger seat.

As another example, the control unit 200 may be configured to receive driving speed information of the vehicle from a third sensing unit 330 for providing driving speed information of the vehicle. In this case, when the driving speed of the vehicle is higher than a set first reference speed, even if the sight line direction of the driver deviates from the set standard (such as the boundary line of the front window or the pillar on one side of the vehicle), the control unit 200 may control the indoor light 500 to the deactivation mode 220.

Here, the first reference speed may be variously determined according to a setting, but generally, it is preferable that the first reference speed is set to a speed that may be considered as a high-speed driving speed. The first reference speed may be set to 60 km/h for a general road, and may be set to 100 km/h for a high-speed road.

If the control unit 200 is not separately provided with information on whether the road is a general road or a high-speed road, it is required that the first reference speed be set to 60 km/h.

The third sensing unit 330 may be a speed sensor for generating driving speed information in the vehicle.

Meanwhile, the control unit 200 may control the mode to the warning mode 230 in a different manner from the deactivation mode 220 described above. As an example thereof, while the sight line direction of the driver deviates from the set standard (such as the boundary line of the front window or the pillar on one side of the vehicle), when the driving speed of the vehicle is higher than a set second reference speed and an obstacle is detected in a driving direction of the vehicle, the control unit 200 may control the indoor light 500 to the warning mode.

To this end, it is required that the control unit 200 be configured to receive obstacle sensing information from a fourth sensing unit 340 for detecting an obstacle in front of or behind the vehicle, as well as receiving the driving speed information of the vehicle from the third sensing unit 330.

Here, the second reference speed is a speed set to be equal to or lower than the first reference speed, but to be considered as a speed higher than a low speed. The second reference speed may be, for example, 30 km/h.

In order to further improve stability, the second reference speed may be set to 5 km/h.

The control of the control unit 200 to the warning mode 230 is performed to alert the driver, when the control unit 200 receives information indicating that an obstacle is detected in a driving direction from the fourth sensing unit 340, in a state where the indoor light 500 is controlled to the activation mode 210 as the sight line direction of the driver deviates from the set standard (such as the boundary line of the front window or the pillar on one side of the vehicle) while the vehicle is driving at a speed lower than the first reference speed.

The warning mode 230 may be performed by repeatedly turning on and off the indoor light as described above.

Meanwhile, the indoor light control system 1000 according to an embodiment of the present invention may include a user input unit 400 for receiving feedback information from the driver.

In addition, the control unit 200 may provide the user with request information for requesting the driver to give feedback information on the control of the indoor light performed by the control unit 200 through the user input unit 400 according to a preset condition, and perform machine learning about the control of the indoor light based on the feedback information input through the user input unit 400 in response thereto.

That is, when driving under the control of the control unit 200 in the above-described various situations is completed, the control unit 200 may be configured to receive information indicating whether the overall control of the control unit 200 is satisfactory or unsatisfactory from the driver, or receive information indicating whether the control of the control unit in a specific control mode or in a specific situation is satisfactory or unsatisfactory from the driver.

Accordingly, a control model may be generated using the feedback information, which derives more detailed and precise situation analysis through a separate deep learning server or the like, and the control model generated in this manner may be applied to the control unit 200 when controlling the indoor light 500.

Meanwhile, in the present invention, the control unit 200 may be configured to maintain the deactivation mode 220 while the vehicle is driving according to a setting, so that the driver is induced to continuously look ahead during driving.

This may be achieved by setting the first reference speed to 0 km/h in the above-described embodiment.

In addition, in the present invention, the control of the indoor light using the control unit 200 may be performed when selected by the driver through the user input unit 400. If the driver does not select the control of the indoor light using the control unit 200, it is required that the driver or another occupant turn on or off the indoor light by performing a separate operation.

In addition, in the present invention, a sensor unit 300 includes the first sensing unit 310, the second sensing unit 320, the third sensing unit 330, and the fourth sensing unit 340, such that the control unit 200 controls the indoor light 500 according to a sight line direction of the driver in various vehicle environments. However, in addition to the above-described four sensing units 310, 320, 330, and 340, the sensor unit 300 may include a sensing unit for providing additional vehicle environment information, if necessary, such that the control unit 200 controls the indoor light appropriately for a current vehicle environment.

Figure 6:
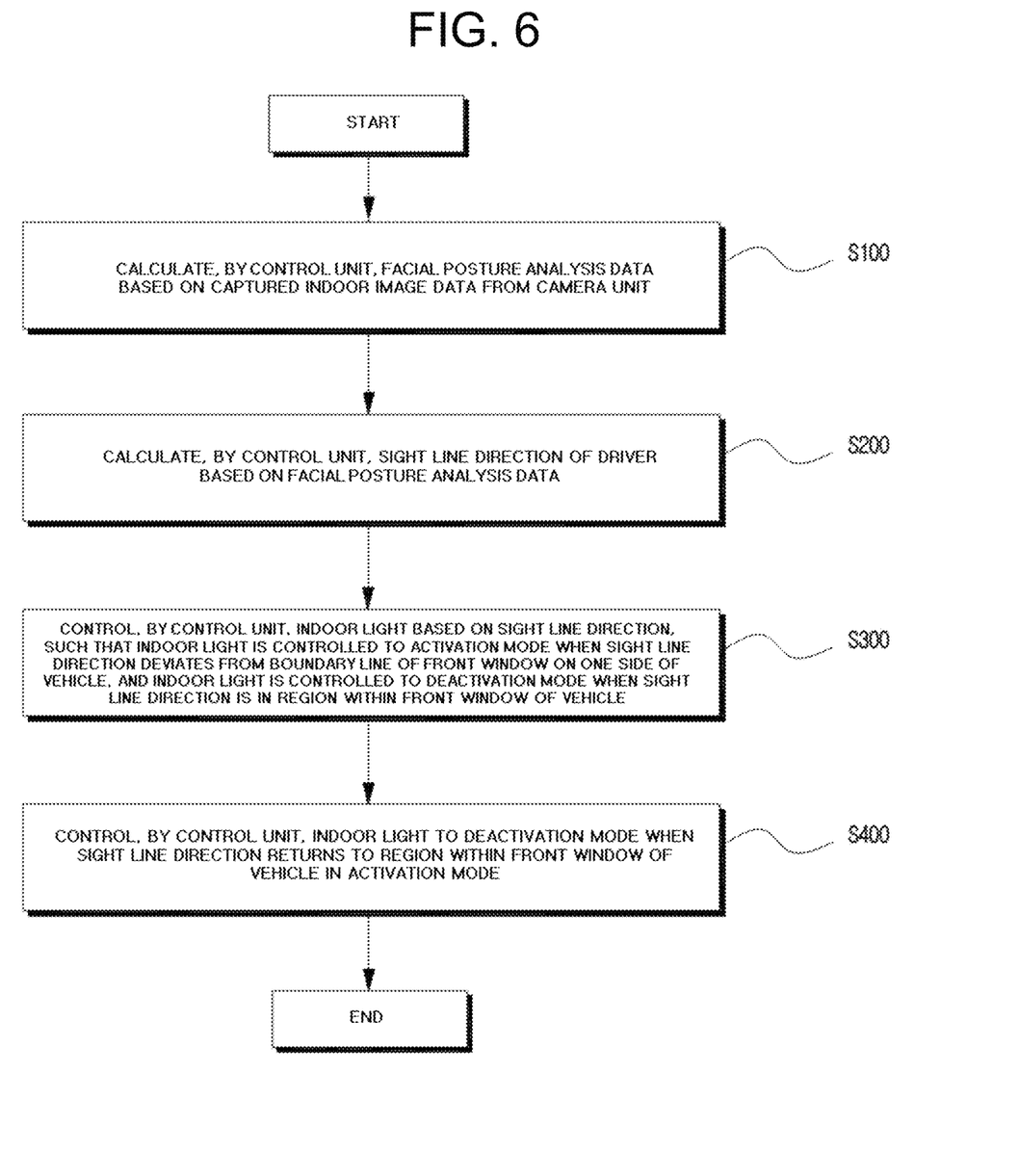
FIG. 6 is a flowchart illustrating a control process of the indoor light control system according to an embodiment of the present invention.
Figure 7:
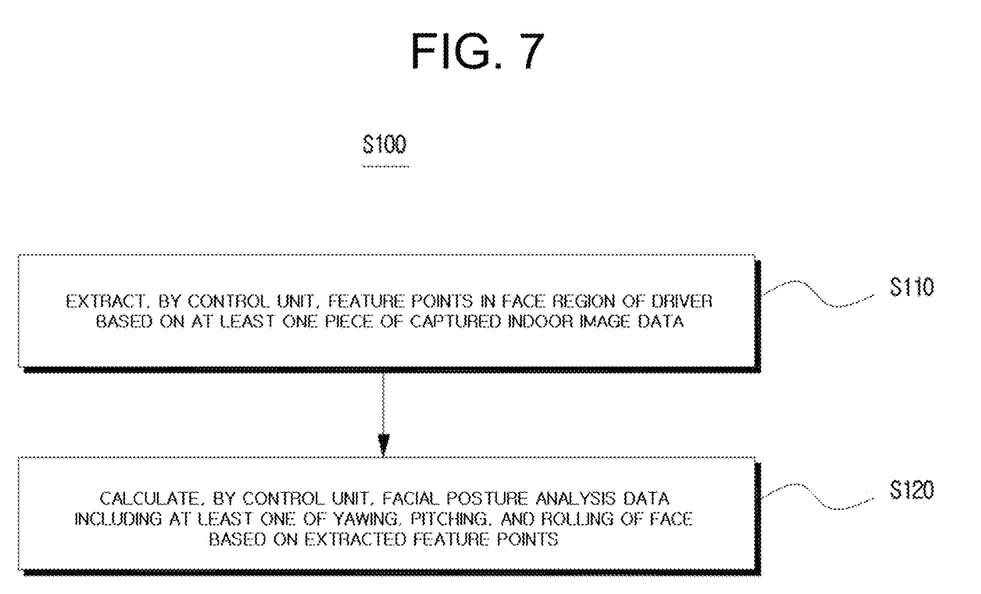
FIG. 7 is a diagram specifically illustrating step S100 of FIG. 6.
Figure 8:
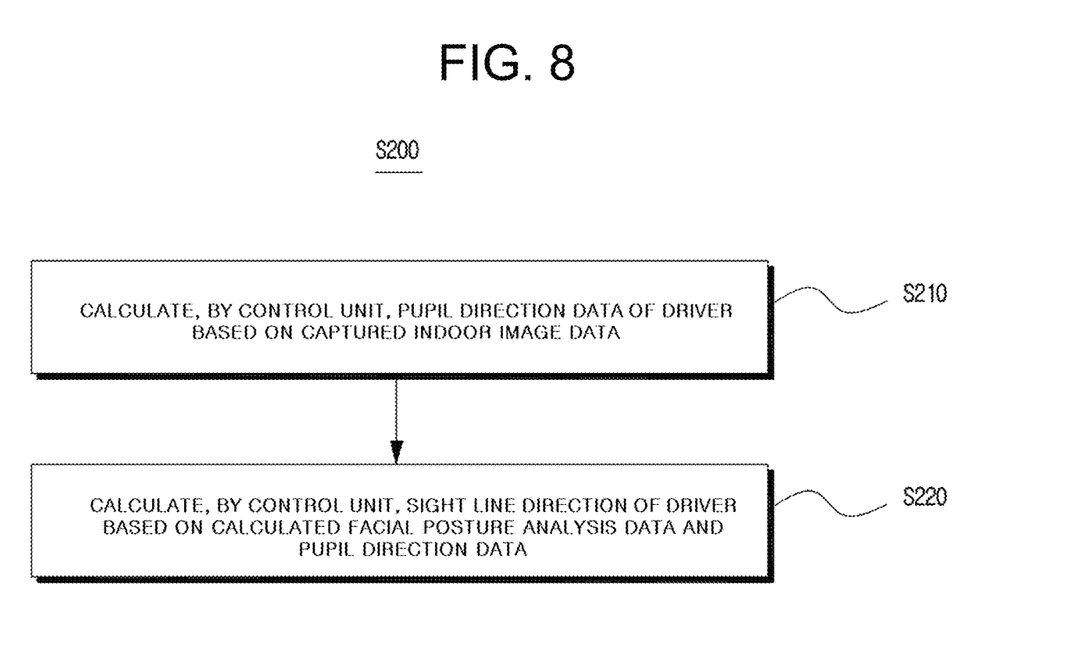
FIG. 8 is a diagram illustrating step S200 of FIG. 6 according to another embodiment of the present invention.

FIG. 6 is a flowchart illustrating a control process of the indoor light control system according to an embodiment of the present invention, FIG. 7 is a diagram specifically illustrating step S100 of FIG. 6, and FIG. 8 is a diagram illustrating step S200 of FIG. 6 according to another embodiment of the present invention.

Referring to the drawings, a control method of the indoor light control system according to an embodiment of the present invention largely includes: calculating, by the control unit 200, facial posture analysis data based on captured indoor image data from the camera unit 100 (S100); calculating, by the control unit 200, a sight line direction of the driver based on the facial posture analysis data (S200); and controlling, by the control unit 200, the indoor light 500 based on the sight line direction SL, such that the indoor light 500 is controlled to an activation mode 210 when the sight line direction deviates from a boundary line of a front window FW on one side of the vehicle, and the indoor light 500 is controlled to a deactivation mode 220 when the sight line direction is in a region within the front window FW of the vehicle.

Here, the step S100 is a step of calculating, by control unit 200, facial posture analysis data based on captured indoor image data transmitted from the camera unit 100 as described above. The step S100 includes: extracting, by control unit 200, feature points in a face region of the driver based on the captured indoor image data (S110); and calculating, by control unit 200, facial posture analysis data including at least one of yawing, pitching, and rolling of a face based on the extracted feature points (S120).

Since the steps S110 and S120 have been described above for the indoor light control system 1000, the description thereof will not be repeated.

In addition, the step S200 is a step of calculating, by control unit 200, a sight line direction of the driver based on the facial posture analysis data. At this time, a forward direction in the calculated facial posture is calculated as the sight line direction of the driver.

In addition, according to another embodiment of the present invention as illustrated in FIG. 8, the calculation of the sight line direction of the driver may include: calculating, by control unit 200, pupil direction data of the driver based on the captured indoor image data (S210); and calculating, by control unit 200, a sight line direction SL of the driver based on the calculated facial posture analysis data and pupil direction data (S220).

This is to more accurately calculate a sight line direction of the driver by additionally considering the pupil direction data of the driver together with the facial posture analysis data when calculating the sight line direction.

Meanwhile, the step S300 is a step of controlling, by control unit 200, the indoor light 500 based on the sight line direction SL, such that the indoor light 500 is controlled to an activation mode 210 when the sight line direction of the driver deviates from a boundary line of a front window FW on one side of the vehicle, and the indoor light 500 is controlled to a deactivation mode 220 when the sight line direction is in a region within the front window FW of the vehicle.

In a state where the indoor light 500 is activated because the sight line direction of the driver deviates from the boundary line of the front window FW on one side of the vehicle, when the sight line direction of the driver returns to the region within the front window FW of the vehicle, the control unit 200 further performs controlling the indoor light to the deactivation mode (S400).

In the present invention, the steps S100 to S300 are continuously performed according to a setting. Therefore, after the step S300, the steps S100 and S200 may be performed again and the indoor light may be operated in the deactivated mode in the step S300. In this case, the step S400 may be included in the step S300.

In addition, in the control method of the indoor light control system according to an embodiment of the present invention, the control unit 200 may control the indoor light to maintain the deactivation mode 220 while the vehicle is driving according to a setting in the step S300, and the driver may select the control of the indoor light using the control unit 200 through the user input unit 400 before the step S100.

In addition, even if the sight line direction deviates from the boundary line of the front window on one side of the vehicle in the step S300, the control unit 200 may exceptionally control the indoor light to the deactivation mode 220. As an example, when an illuminance in the vehicle is higher than a set reference illuminance or a driving speed of the vehicle is higher than a set first reference speed, the indoor light may be controlled to the deactivation mode 220.

In these embodiments, in a case where a current indoor illuminance in the vehicle is higher than the reference illuminance, that is, during daytime rather than at night or when the weather is cloudy, even though the indoor light is activated, this is not helpful in securing driver's visibility. Therefore, in this case, it is preferable that the indoor light is controlled to the deactivation mode.

In addition, even if the sight line direction deviates from the boundary line of the front window on one side of the vehicle in the step S300, when there is an occupant on a front passenger seat as a result of determining whether or not there is an occupant on a front passenger seat based on captured indoor image data or seat weight sensing data, and the sight line direction is within a preset front passenger seat direction range, the control unit 200 may control the indoor light to the deactivation mode.

Furthermore, even if the sight line direction deviates from the boundary line of the front window on one side of the vehicle in the step S300, when a turn signal lamp on one side of the front window of the vehicle is turned on, and the sight line direction is in a region within a side mirror on the one side of the front window of the vehicle, the control unit 200 may control the indoor light to the deactivation mode.

In addition, when a current driving speed of the vehicle is higher than the first reference speed (for example, when the driving speed of the vehicle is higher than 60 km/h), if the driver gazes at a front passenger seat or a rear seat even for a short period of time, this may pose a threat to driving safety. Therefore, in this case, it is preferable that the indoor light 500 is controlled to the deactivation mode 220, such that the driver is induced to gaze ahead.

In addition, as described above for the indoor light control system 1000, when a current driving speed of the vehicle is higher than the second reference speed (for example, when the current driving speed of the vehicle is higher than 30 km/h), since the current driving speed is lower than the first reference speed, the control unit 200 controls the indoor light 500 to the activation mode 210. However, at this time, when an obstacle is detected through an obstacle detecting device such as a front radar, the indoor light 500 may be controlled to the warning mode 230.

In the warning mode 230, the control unit 200 repeatedly turns on and off the indoor light 500 at predetermined intervals to alert the driver.

Here, it is preferable that the second reference speed is equal to or lower than the first reference speed.

A program for executing a method according to an embodiment of the present invention may be recorded in a computer-readable recording medium.

The computer-readable medium may include program instructions, data files, data structures, and the like either alone or in combination. The medium may be specially designed and configured, or may be known for use by those skilled in computer software.

Examples of computer-readable recording media include magnetic media such as hard disks, floppy disks, and magnetic tapes, optical recording media such as CD-ROMs and DVDs, magneto-optical media such as floptical disks, and hardware devices specially configured to store and execute program instructions such as ROMs, RAMs, and flash memories. Here, the medium may be a transmission medium such as light including a carrier wave for transmitting a signal specifying a program command, a data structure, or the like, a metal wire, or a waveguide.

What is claimed is:

1. An indoor light control system for controlling at least one indoor light provided in a vehicle, the indoor light control system comprising:
    a camera unit adapted to provide captured indoor image data of the vehicle; and
    a control unit adapted to control the indoor light based on the captured indoor image data,
    wherein the control unit is adapted to calculate a sight line direction of a driver siting on a driver's seat based on the captured indoor image data, and control the indoor light according to the sight line direction of the driver;
    wherein the control unit is adapted to:
        extract feature points in a face region of the driver based on the captured indoor image data;
        calculate facial posture analysis data including at least one of yawing, pitching, and rolling of a face based on the extracted feature points;
        calculate the sight line direction of the driver based on the facial posture analysis data;
        calculate pupil direction data of the driver based on the captured indoor image data; and calculate a sight line direction of the driver based on the calculated facial posture analysis data and pupil direction data.

2. The indoor light control system of claim 1, wherein the control unit is adapted to calculate a forward direction of the face as the sight line direction of the driver based on the facial posture analysis data.

3. The indoor light control system of claim 2, wherein the control unit is adapted to:
control the indoor light to an activation mode when the sight line direction deviates from a boundary line of a front window on one side of the vehicle, and
control the indoor light to a deactivation mode when the sight line direction returns to a region within the front window of the vehicle.

4. The indoor light control system of claim 3, wherein when an illuminance in the vehicle is higher than a set reference illuminance, the control unit is adapted to control the indoor light to the deactivation mode even if the sight line direction deviates from the boundary line of the front window on one side of the vehicle.

5. The indoor light control system of claim 3, wherein when a turn signal lamp on one side of the front window of the vehicle is turned on, and the sight line direction is in a region within a side mirror on the one side of the front window of the vehicle, the control unit is adapted to control the indoor light to the deactivation mode.

6. The indoor light control system of claim 3, wherein the control unit is adapted to determine whether or not there is an occupant on a front passenger seat based on at least one of the captured indoor image data or seat weight sensing data, and control the indoor light to the deactivation mode when the sight line direction is within a preset front passenger seat direction range in a case where there is an occupant on the front passenger seat.

7. The indoor light control system of claim 3, wherein when a driving speed of the vehicle is higher than a set first reference speed, the control unit is adapted to control the indoor light to the deactivation mode.

8. The indoor light control system of claim 7, wherein when the sight line direction deviates from the boundary line of the front window on one side of the vehicle, the driving speed of the vehicle is higher than a set second reference speed, and an obstacle is detected in a driving direction of the vehicle, the control unit is adapted to control the indoor light to a warning mode, and
the second reference speed is equal to or lower than the first reference speed.

9. A control method of an indoor light control system, the indoor light control system comprising: a camera unit adapted to provide captured indoor image data of the vehicle; and a control unit adapted to control the indoor light based on the captured indoor image data, calculate a sight line direction of a driver siting on a driver's seat based on the captured indoor image data, and control the indoor light according to the sight line direction of the driver, the control method comprising:
a) calculating, by the control unit, facial posture analysis data based on captured indoor image data from the camera unit;
b) calculating, by the control unit, a sight line direction of the driver based on the facial posture analysis data; and
c) controlling, by the control unit, the indoor light based on the sight line direction, such that the indoor light is controlled to an activation mode when the sight line direction deviates from a boundary line of a front window on one side of the vehicle, and the indoor light is controlled to a deactivation mode when the sight line direction is in a region within the front window of the vehicle.

10. The control method of claim 9, wherein step a) comprises:
extracting, by the control unit, feature points in a face region of the driver based on the captured indoor image data; and
calculating, by the control unit, facial posture analysis data including at least one of yawing, pitching, and rolling of a face based on the extracted feature points.

11. The control method of claim 9, wherein step b) comprises:
calculating, by the control unit, pupil direction data of the driver based on the captured indoor image data; and
calculating, by the control unit, a sight line direction of the driver based on the calculated facial posture analysis data and pupil direction data.

12. The control method of claim 11, further comprising, after controlling the indoor light to the activation mode in step c), controlling, by the control unit, the indoor light to the deactivation mode when the sight line direction returns to the region within the front window of the vehicle.

13. The control method of claim 11, wherein in step c), while the sight line direction deviates from the boundary line of the front window on one side of the vehicle, when an illuminance in the vehicle is higher than a set reference illuminance or when a driving speed of the vehicle is higher than a set first reference speed, the control unit controls the indoor light to the deactivation mode.

14. The control method of claim 9, wherein in step b), the control unit calculates a forward direction of the face as the sight line direction of the driver based on the calculated facial posture analysis data.

15. The control method of claim 11, wherein in step c), while the sight line direction deviates from the boundary line of the front window on one side of the vehicle, when a turn signal lamp on one side of the front window of the vehicle is turned on, and the sight line direction is in a region within a side mirror on the one side of the front window of the vehicle, the control unit controls the indoor light to the deactivation mode.

16. The control method of claim 11, wherein in step c), while the sight line direction deviates from the boundary line of the front window on one side of the vehicle, when there is an occupant on a front passenger seat as a result of determining whether or not there is an occupant on a front passenger seat based on the captured indoor image data or seat weight sensing data, and the sight line direction is within a preset front passenger seat direction range, the control unit controls the indoor light to the deactivation mode.

17. The control method of claim 13, wherein in step c), while the sight line direction deviates from the boundary line of the front window on one side of the vehicle, when the driving speed of the vehicle is higher than a set second reference speed, and an obstacle is detected in a driving direction of the vehicle, the control unit controls the indoor light to a warning mode, and
the second reference speed is equal to or lower than the first reference speed.

18. A computer-readable recording medium storing a program comprising instructions for executing a control method of an indoor light control system, the indoor light control system comprising: a camera unit adapted to provide captured indoor image data of the vehicle; and a control unit adapted to control the indoor light based on the captured indoor image data, calculate a sight line direction of a driver siting on a driver's seat based on the captured indoor image data, and control the indoor light according to the sight line direction of the driver, the control method comprising:

a) calculating, by the control unit, facial posture analysis data based on captured indoor image data from the camera unit;

b) calculating, by the control unit, a sight line direction of the driver based on the facial posture analysis data; and     c) controlling, by the control unit, the indoor light based on the sight line direction, such that the indoor light is controlled to an activation mode when the sight line direction deviates from a boundary line of a front window on one side of the vehicle, and the indoor light is controlled to a deactivation mode when the sight line direction is in a region within the front window of the vehicle.

19. The computer-readable recording medium of claim 18, wherein step a) comprises:

extracting, by the control unit, feature points in a face region of the driver based on the captured indoor image data; and     calculating, by the control unit, facial posture analysis data including at least one of yawing, pitching, and rolling of a face based on the extracted feature points.

20. The computer-readable recording medium of claim 18, wherein step b) comprises:

calculating, by the control unit, pupil direction data of the driver based on the captured indoor image data; and     calculating, by the control unit, a sight line direction of the driver based on the calculated facial posture analysis data and pupil direction data.

\* \* \* \* \*